(12) United States Patent
    Keskar

(10) Patent No.: US 12,653,446 B2
(45) Date of Patent: Jun. 16, 2026

(54) SYSTEM AND METHOD FOR MEASURING PROGRESSION OF PARKINSON'S DISEASE USING WEARABLES

(71) Applicant: Jui Keskar, Pune (IN)

(72) Inventor: Jui Keskar, Pune (IN)

(73) Assignee: Jui Keskar, Pune (IN)

( * ) Notice: Subject to any disclaimer, the term of this patent is extended or adjusted under 35 U.S.C. 154(b) by 227 days.

(21) Appl. No.: 18/214,531

(22) Filed: Jun. 27, 2023

(65) Prior Publication Data

US 2024/0180478 A1     Jun. 6, 2024

Related U.S. Application Data

(60) Provisional application No. 63/430,116, filed on Dec. 5, 2022.

(51) Int. Cl.
    *A61B 5/00*      (2006.01)
    *A61B 5/11*      (2006.01)
    *G16H 10/60*     (2018.01)

(52) U.S. Cl.
    CPC .......... *A61B 5/4082* (2013.01); *A61B 5/1101* (2013.01); *A61B 5/1114* (2013.01); *A61B 5/112* (2013.01); *A61B 5/4803* (2013.01); *A61B 5/4842* (2013.01); *G16H 10/60* (2018.01)

(58) Field of Classification Search
    CPC ... A61B 5/4082; A61B 5/1101; A61B 5/1114; A61B 5/112; A61B 5/4803; A61B 5/4842
    See application file for complete search history.

(56) References Cited

U.S. PATENT DOCUMENTS

| | | | |
|---|---|---|---|
| 2007/0112393 A1* | 5/2007 | Gliner ................ | A61N 1/36067 607/45 |
| 2015/0157274 A1* | 6/2015 | Ghassemzadeh .... | A61B 5/7275 600/595 |
| 2015/0164377 A1* | 6/2015 | Nathan ................ | A61B 5/6802 600/595 |

* cited by examiner

*Primary Examiner* — Sana Sahand
(74) *Attorney, Agent, or Firm* — Nicholas Palacio

(57)         ABSTRACT

Disclosed is a system and method for tracking progression of Parkinson's Disease using a plurality of wearables worn by a patient. The real time data from the plurality of wearables is used to calculate a progression index for Parkinson's Disease based on Slowness/Stiffness, Tremor profiling, Gait changes and speech distortions. The progression index determines the stage of Parkinson's Disease based on intensity of symptoms mentioned above. The results are shared with a medical professional for evaluating current treatment strategies.

6 Claims, 4 Drawing Sheets

110

Controller

102

104

108

Cloud

106

112

100

$(x_1, y_1, z_1)$ $(x_2, y_2, z_2)$ $(x_3, y_3, z_3)$

SYSTEM AND METHOD FOR MEASURING PROGRESSION OF PARKINSON'S DISEASE USING WEARABLES

TECHNICAL FIELD

The present invention relates generally to medical devices and specifically to a system and method for measuring progression of Parkinson's disease using wearables.

BACKGROUND

Human body is susceptible to several neurological disorders with Parkinson's Disease being one of the most prevalent one. Parkinson's Disease result in patients suffers from stiffening of body, tremors of limbs, hands, or other body parts, gait disorders, speech distortion. Parkinson's progression is usually quite gradual as it is a progressive illness, with symptoms slowly growing worse over time. For every patient, Parkinson's Disease has a distinct pattern of progression. It is essential that relevant interventions are administered based on current progression level of Parkinson's Disease. Primarily, the progression of disease can be broken down into mild, moderate and advanced stages. Accurate information about the level of clinical disability can lead to timely interventions and improvement in quality of life for the patients.

Conventionally, patient's attendants tune the brain pacemaker as per his/her gut feeling or based on patient testimony. Further, even in a clinical setting, medical professionals generally rely on their perception for evaluating progression and offer distinct medication based on their subjective understanding. Further, there are a number of scales are used to measure progression in Parkinson's, for example the Hoehn and Yahr scale which categorises the severity of motor symptoms based on how they affect an individual's mobility.

One of the glaring limitations of said conventional methods mentioned above is the lack of technical and objective criteria. The rating scales are primarily questionnaires and are evaluated based on patient responses, which is subjective thereby resulting in trial and error in dosage planning. Moreover, none of the existing setup for measuring progression of Parkinson's Disease can be implemented in a home setup as they are meant for clinical settings.

In light of the above-mentioned problems associated with existing methods for tracking progression of Parkinson's Disease, it is highly desirable to have a method for tracking progression of Parkinson's Disease in a patient in order to evaluate treatment and management strategies. Consequently, the present invention provides a system and method to measure progression of Parkinson's Disease using wearables.

SUMMARY

Embodiments of the present disclosure present technological improvements as solutions to one or more of the above-mentioned technical problems recognized by the inventor in conventional solutions.

The present invention discloses a system and method for tracking progression of Parkinson's Disease using a plurality of wearables worn by a patient. The real time data from the plurality of wearables is used to calculate a progression index for Parkinson's Disease based on Slowness/Stiffness, Tremor profiling, Gait changes and speech distortions. The progression index determines a stage of Parkinson's Disease based on intensity of symptoms mentioned above. The results are shared with a medical professional for evaluating current treatment strategies and dosage planning.

Additional aspects, advantages, features and objects of the present disclosure would be made apparent from the drawings and the detailed description of the illustrative embodiments construed in conjunction with the complete specification that will follow.

It will be appreciated that features of the present disclosure are susceptible to being combined in various combinations without departing from the scope of the present disclosure.

OBJECT OF THE INVENTION

An object of the present invention is to provide a method and system for measuring progression of Parkinson's disease in a subject.

Another object of the present invention is to provide a method for dosage planning and clinical monitoring of the subject in a home setup.

Another object of the present invention is remotely provide clinical insights pertaining to a disease condition of the subject.

BRIEF DESCRIPTION OF DRAWINGS

The summary above, as well as the following description of illustrative embodiments are better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

It will be appreciated that the drawings illustrated herein are for representation purposes only and do not intend to limit the scope of the present disclosure, and actual implementation of the present disclosure may be viewed substantially differently.

DESCRIPTION OF EMBODIMENTS

The following description illustrates embodiments of the present disclosure and ways in which they can be implemented. Although some modes of carrying out the present disclosure have been disclosed, those skilled in the art would recognize that other embodiments for carrying out or practicing the present disclosure are also possible.

Parkinson's disease, a neurodegenerative disorder, manifests in a range of debilitating symptoms that profoundly impact a person's motor and speech abilities. Among the most prominent and consistent signs observed in all patients are slowness or stiffness of the arms, gait changes, speech distortion, and tremors. These four hallmark symptoms serve as crucial indicators for diagnosing and assessing the progression of Parkinson's disease. The manifestation of arm slowness or stiffness is characterized by a notable decrease in dexterity, making simple tasks such as writing, buttoning a shirt, or even lifting objects challenging and time-consuming. Gait changes, on the other hand, refer to alterations in the way individuals walk, often leading to a shuffling gait, reduced stride length, and difficulty initiating or stopping movement. Speech distortion presents itself as a decline in vocal control and articulation, causing patients to experience slurred speech, a monotonous tone, or a softer voice. Lastly, tremors, which are often one of the most recognizable symptoms, involve involuntary rhythmic shaking or trembling of various body parts, commonly affecting the hands, fingers, or limbs. By closely monitoring and evaluating the severity and progression of these four core symptoms, medical professionals can gain valuable insights into the specific stage of Parkinson's disease a patient may be experiencing. This information enables the development of tailored treatment plans, the assessment of medication efficacy, and the implementation of strategies to improve the individual's quality of life.

Figure 1:
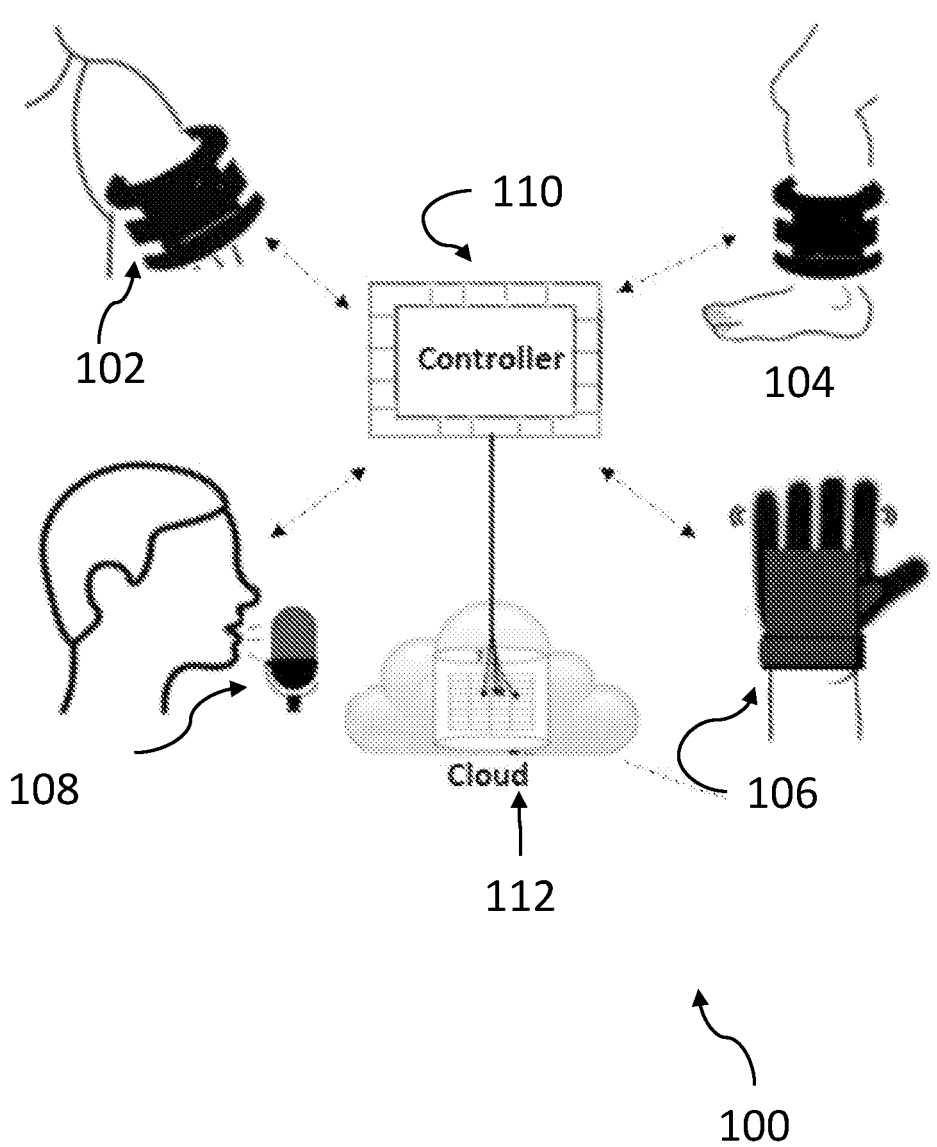
FIG. 1 depicts a system for tracking progression of Parkinson's disease using wearables as per the disclosed invention.

FIG. 1 depicts an exemplary system 100 as per the present disclosure. The system 100 comprises a patient wearing an arm strap device 102, a leg strap device 104 and a hand glove device 106. The system 100 further comprises a speech distortion unit 108, a controller 110 and a cloud server 112. The arm strap device 102 monitors slowness/stiffness of upper arm through the movement speed and extent of movement. The leg strap device 104 monitors gait changes in walking patterns of the patient. The hand glove device 106 is used for tremor profiling and thereby, measuring an intensity and frequency of tremors. The speech distortion unit 108 measures accuracy of word pronunciation and speed of speech in patient suffering from Parkinson's Disease. The controller 110 is communicably coupled to each of the arm strap device 102, leg strap device 104, the hand glove device 106 and the cloud server 112.

As per a preferred embodiment of the present invention, the patient wears the arm strap device 102 on atleast one of the upper arms. Further, the patient wears the leg strap device 104 on atleast one of the lower legs. Furthermore, the patient wears the hand glove device 106 on atleast one of the hand palms. The speech distortion unit 108 is contained within the controller 110. The controller 110 is stored within a housing frame 114 thereby protecting the controller circuitry from damage.

Figure 2:
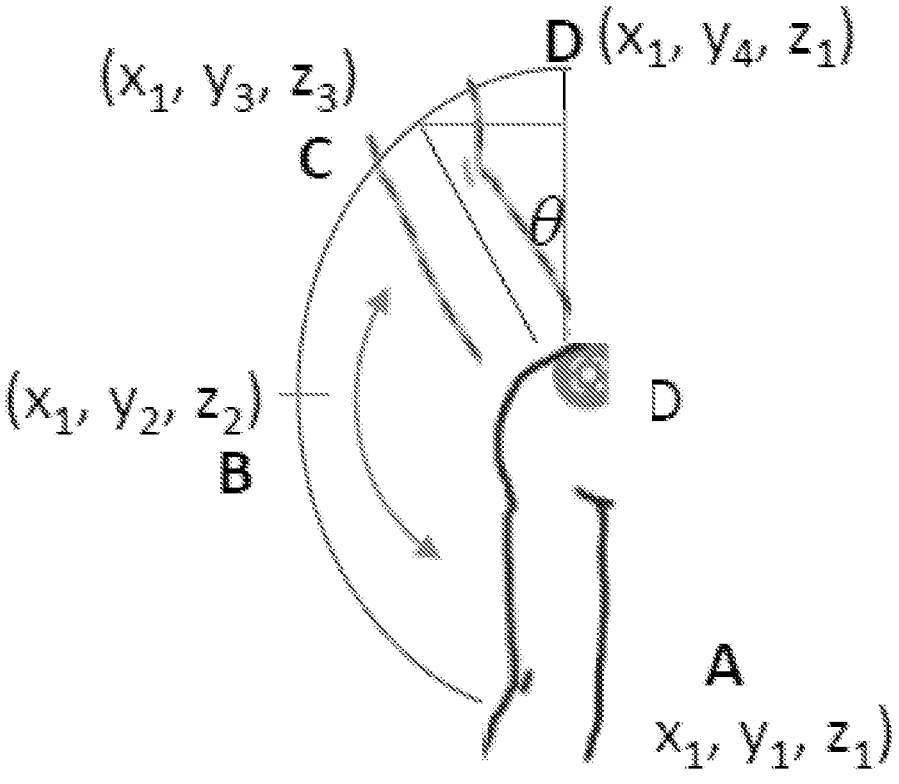
FIG. 2 depicts an arm movement recorded by an arm strap device.

The arm strap device 102 is wearable on either of the upper arms of the patient. The arm strap device 102 comprises one or more sensors operable to capture location coordinates of the arm position of the patient, during an arm movement, in real time and transmit the captured coordinates to the controller 110. The arm strap device 102 enables computation, by the controller 110, of a stiffness index for the patient with Parkinson's disease wherein the stiffness index corresponds to changes in extent and speed of movement as compared to healthy person. In a preferred embodiment, the patient with the arm strap device 102 strapped on one of the upper arms moves his arm from a low point to a high point and vice versa. The one or more sensors record the said movement of upper arm of the patient by capturing location coordinates of arm position from the low point till the high point through atleast two intermediate points, as well the angle of movement of the arm of the patient. The controller 110 receives x,y,z coordinates for arm position throughout the arm movement from the low point to the high point as well as angle of arm movement at each arm position. The controller 110 computes the slowness index for the patient with Parkinson's disease by comparing the time taken for arm movement from the low point to the high point by a person with Parkinson's disease as against the time taken for said arm movement by a healthy person. The arm movement recorded by the arm strap device 102 is done relative to the controller 110 wherein the controller 110 is placed on the body of the patient. The stiffness index computed by the controller 110 is averaged over atleast 10 arm movements. FIG. 2 depicts an arm movement recorded by the arm strap device 102. The stiffness index is calculated as follows:

$$\text{stiffness index} = \left[ \frac{\pi * t1}{(\pi - \theta) * t_0} - 1 \right] * 100$$

wherein:
  $t0$=Time taken by normal person for A-B-C-D trajectory
  $t1$=Time taken by PD patient. It is time diff between min & max values of y-coordinates
  Angle skipped by patient while lifting hand, $\theta = \sin -1(|z3 - z1|/r0)$
  $z1$ and $z3$ are z-coordinates at min and max values of y-coordinates
  $r0 = |y2 - y1|$. is the radius of device trajectory (A-B-C).
  $y1$ and $y3$ are y-coordinates at min and max values of z-coordinates The stiffness index computed by the controller 110, based on the arm movement recorded by the arm strap device 102, is applicable to the respective arm on which the arm strap device 102 is strapped onto. In another embodiment, the patient may wear the arm strap device 102 on both the arms so that the stiffness index is captured for both the arms. Optionally, once the arm movement recording is completed for one of the arms and the stiffness index is computed by the controller 110, the arm strap device 102 can be switched onto the other arm, and the stiffness index may be computed for the other arm in a similar manner. In a preferred embodiment of the present invention, the stiffness index is a numerical value in the range of 0-20.

Figure 3:
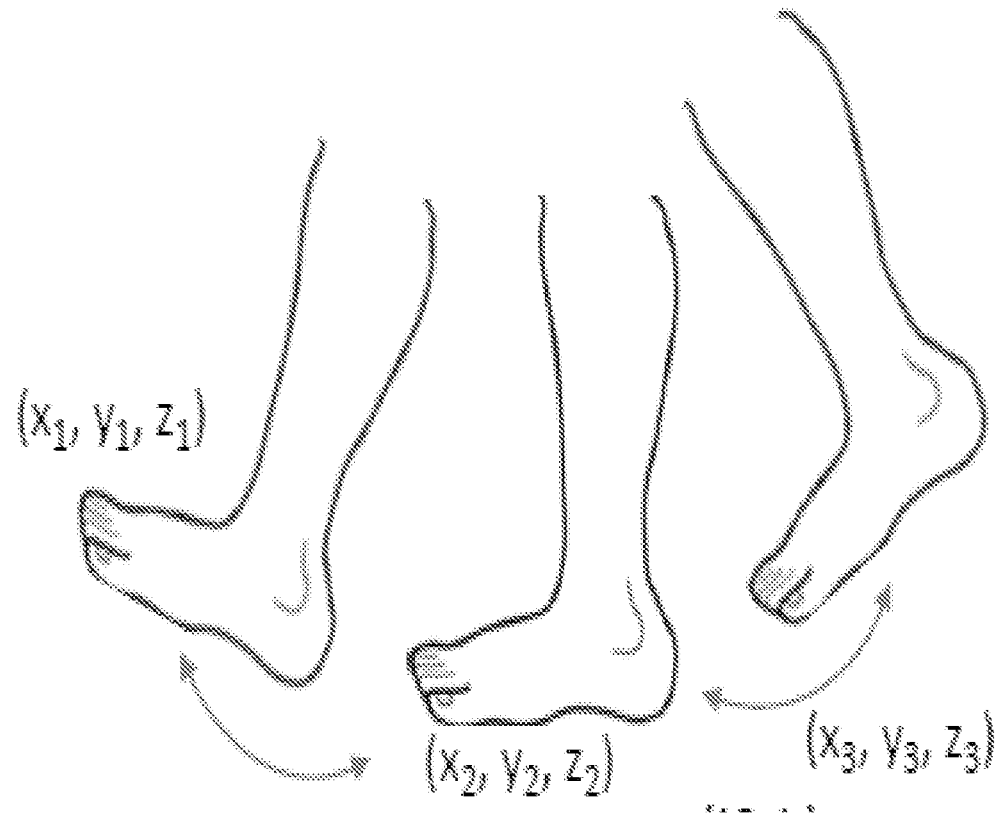
FIG. 3 depicts a leg movement recorded by a leg strap device.

The leg strap device 104 is wearable on either of the lower leg of the patient. The leg strap device 104 comprises one or more sensors operable to capture location coordinates of the leg position, during a leg movement, in real time and transmit the captured coordinates to the controller 110. The leg strap device 104 enables computation, by the controller 110, of a gait index for patient wherein the gait index corresponds to changes in manner of walking and ability to move the body as compared to a healthy person. In a preferred embodiment, the patient with the leg strap device 104 strapped on one of the lower legs moves his leg from a farthest point to a back farthest point and vice versa. The one or more sensors record the said movement of lower leg of the patient by capturing location coordinates of leg position from the farthest point till the back farthest point through an on-ground point. The controller 110 receives x,y,z coordinates for leg position throughout the leg movement from the farthest point to the back farthest point. The controller 110 computes the gait index for the patient by calculating an offset in each step as the leg movement in early phases of disease in the said patient. The leg movement recorded by the leg strap device 104 is done relative to the controller 110 placed on the body of the patient. The gait index computed by the controller 110 is averaged over atleast 10 steps thrice a day. FIG. 3 depicts a leg movement recorder by a leg strap device.

The gait index is calculated as follows:

$$\text{gait index} = \frac{\sum_{i=0}^{i=3} \sqrt{(x_i' - x_i)^2 + (y_i' - y_i)^2 + (z_i' - z_i)^2}}{\sqrt{(x_1 - x_3)^2 + (y_1 - y_3)^2 + (z_1 - z_3)^2}}$$

wherein:

$x_i$, $y_i$, $z_i$ are coordinates of PD patient leg while walking (front farthest, on ground and back farthest positions);

$x_i'$, $y_i'$, $z_i'$ are step coordinates during early phases

The gait index computed by the controller 110, based on the leg movement recorded by the leg strap device 104, is applicable to the respective leg on which the leg strap device 104 is strapped onto. In another embodiment, the patient may wear the leg strap device 104 on both the legs so that the gait index is captured for both the legs. Optionally, once the leg movement recording is completed for one of the legs and the gait index is computed by the controller 110, the leg strap device 104 can be switched onto the other leg, and the gait index may be computed for the other leg in a similar manner. In a preferred embodiment of the present invention, the gait index is a numerical value in the range of 0-20.

The hand glove device 106 comprises one or more sensors operable to capture location coordinates of the palm position of the patient, during a tremulous activity, in real time and transmit the captured coordinates to the controller 110. The hand gloves device 106 is operable to compute a tremor index for a limb of patient with Parkinson's disease wherein the tremor index corresponds to intensity and frequency of tremulous activity experienced by the patient. The one or more sensors record the movement of palm of the patient during the tremulous activity. The controller 110 receives x,y,z coordinates for palm position throughout the palm movement during the tremulous activity and computes the tremor index for the patient with Parkinson's disease. The palm movement recorded by the hand gloves device 106 is done relative to the controller 110 placed on the body of the patient. The tremor index can be categorised into a one of low, medium and high levels based on a predefined threshold.

The tremor index computed by the controller 110, based on the palm movement recorded by the hand glove device 106, is applicable to the respective palm on which the hand glove device 106 is strapped onto. In another embodiment, the patient may wear the hand glove device 106 on both the palms so that the tremor index is captured for both the palms. Optionally, once the tremors recording is completed for one of the palms and the tremor index is computed by the controller 110, the hand glove device 106 can be switched onto the other palm, and the tremor index may be computed for the other palm in a similar manner. In a preferred embodiment of the present invention, the stiffness index is a numerical value in the range of 0-300.

The speech distortion unit 108 calculates distortion in speech uttered by the patient. The speech distortion unit 108 digitizes a patient speech and compares the digitized patient speech with a model digitized speech. Based on the said comparison, the speech distortion unit 108 computes a speech index by computing a degree of similarity between the digitized patient speech and model digitized speech. Speech Index depicts a speech distortion percentage wherein the speech distortion refers to number of words distorted in a standard sentence against the total number of words in the sentence. The speech distortion further undertakes the time taken to speak the complete sentence. The speech index computed by the speech distortion unit 108 is averaged over atleast 3 sentences. In a preferred embodiment of the present invention, the stiffness 5 index is a numerical value in the range of 0-30.

Figure 4:
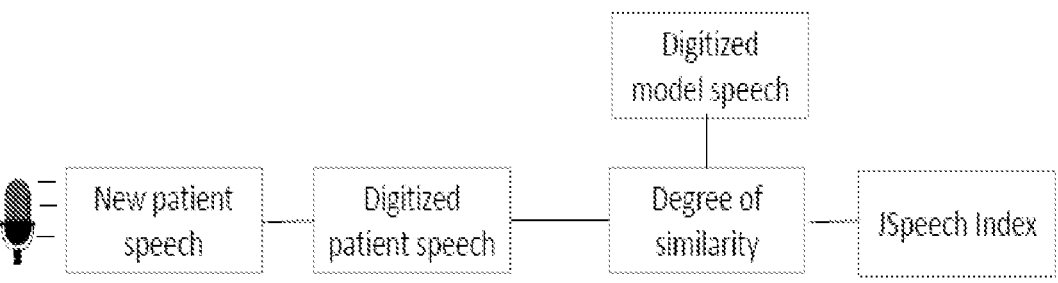
FIG. 4 depicts a block diagram for calculation of speech index.

In a preferred embodiment, the speech distortion unit 108 is incorporated within the controller 110. FIG. 4 depicts a block diagram for calculation of speech index.

In operation, a patient wears the arm strap device 102 on the upper arm, the leg strap device 104 on lower leg, a hand gloves device 106 on palm and a controller 110 around the central waist portion. The patient moves the arm from a low point to high point and the controller 110 computes a stiffness index. Further, the patient moves the leg from the farthest point to a back farthest point, and the controller 110 computes a gait index. Furthermore, the controller 110 computes a tremor index for tremulous activity experienced by the patient. The patient then utters a speech, and the speech distortion unit 108 computes a speech index. Based on the said stiffness index, gait index, tremor index and speech index, the controller 110 computes a disease progression index wherein the disease progression index depicts a current stage of Parkinson's disease in the patient. In a preferred embodiment, the disease progression index is computed as follows:

Disease Progression Index =

$$\text{tremor index} * \left[1 + \frac{\text{stiffness index}}{100}\right] * \left[1 + \frac{\text{gait index}}{100}\right] * \left[1 + \frac{\text{speech index}}{100}\right]$$

In a preferred embodiment of the present invention, the Disease progression Index is a numerical value in the range of 0-550.

In yet another embodiment, the disease progression index can be categorised into one or more progression stages based on empirical data for disease progression indexes across one or more stages of Parkinson's disease.

Optionally, the controller 110 is operable to build a Disease progression profile for the patient wherein the Disease progression profile comprises historical data as well as current findings along with a disease progression curve generated from Disease progression Index over a period of time.

In another aspect of the present invention, the controller 110 is operable to communicate with an application software accessible through a web browser or a mobile application over a data communication network wherein the application software stores the current readings for stiffness index, gait index, speech index, tremor index and the disease progression index for a given patient. Further, the application software stores the Disease progression profile for each patient wherein each patient is assigned a unique patient id. The application software is accessible by a medical professional thereby allowing the medical professional to remotely access the readings and analyze the current stage of progression of Parkinson's disease for the said patient. This results in adjustments, if any in the present treatment strategy, medications and dosage planning for the patient.

In yet another embodiment of the present invention, the controller 110 is operable to calculate settings for a DBS (Deep brain Stimulator) pacemaker based on the current Disease Progression Profile which is subsequently used by a caregiver to tune the DBS pacemaker.

The data communication network may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of the foregoing.

As described herein, the controller 110 is a processor that includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a controller using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer or other suitable display for providing any of the results mentioned herein to a user.

One or more components of the invention are described as unit or modules for the understanding of the specification. For example, a unit may include self-contained component in a hardware circuit comprising of logical gate, semiconductor device, integrated circuits or any other discrete component. The unit may also be a part of any software programme executed by any hardware entity for example processor. The implementation of unit as a software programme may include a set of logical instructions to be executed by a processor or any other hardware entity.

Additional or less units can be included without deviating from the novel art of this disclosure. In addition, each unit can include any number and combination of sub-units, and systems, implemented with any combination of hardware and/or software units.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

I claim:

1. A system for measuring progression of Parkinson's disease in a patient, the system comprising:

a controller strapped onto the patient's body and configured to receive location coordinates from:

an arm strap device strapped on to at least one arm of the patient wherein the arm strap device comprises one or more sensors configured to capture location coordinates of an arm movement of the patient;

a leg strap device strapped on to at least one leg of the patient wherein the leg strap device comprises one or more sensors configured to capture location coordinates of a leg movement of the patient;

a hand glove device strapped on to at least one palm of the patient wherein the hand glove device comprises one or more sensors configured to capture location coordinates of a palm movement during a tremulous activity experienced by the patient;

a speech distortion unit operable to record and digitize speech to determine distortion in speech uttered by the patient;

an application software communicably coupled with the controller through a data communication network;

wherein the controller is operable to compute a stiffness index based on the location coordinates pertaining to the arm movement of the patient and according to the formula:

$$stiffnessindex = \left[ \frac{\pi * t1}{(\pi - \theta) * t_0} \right] * 100$$

wherein r1 is a trajectory radius of the arm movement from a low point to a high point;

t$\theta$ is a time taken by the patient to complete the arm movement from the low point to the high point;

t0 is a reference time taken by a normal person to complete a corresponding arm movement;

$\theta$ is an angular displacement of the arm movement;

wherein the controller is operable to compute a gait index for the patient based on the location coordinates pertaining to the leg movement of the patient and according to the formula:

$$gaitindex = = \frac{\sum_{i=1}^{i=3} \sqrt{(x_i' - xi)^2 + (y_i' - yi)^2 + (z_i' - zi)^2}}{\sqrt{(x_1 - x_3)^2 + (y_1 - y_3)^2 + (z_1 - z_3)^2}}$$

wherein xi, yi, zi are coordinates of PD patient leg while walking (front farthest, on ground and back farthest positions);

xi', yi', zi' are step coordinates during early phases;

y1 and y3 are y-coordinates at min and max values of z-coordinates z1 and z3 are z-coordinates at min and max values of y-coordinates;

wherein the controller is operable to compute a tremor index for the patient based on on intensity and frequency of the palm movement during tremulous activity experienced by the patient;

wherein the controller is operable to compute a speech index for the patient based on the the digitized speech pertaining to the distortion in speech uttered by the patient and wherein computing the speech index comprises:

comparing the digitized speech from the patient with a model digitized speech;

computing a degree of similarity between the digitized speech and the model digitized speech; and generating a numerical value for the speech index value representing a percentage of speech distortion; and wherein the controller is operable to compute a disease progression index for the patient based on the stiffness index, gait index, tremor index and speech index, wherein the disease progression index is computed according to the formula:

$$DiseaseProgressionIndex =$$

$$tremorindex * \left[1 + \frac{stiffnessindex}{100}\right] * \left[1 + \frac{gaitindex}{100}\right] * \left[1 + \frac{speechindex}{100}\right]$$

and wherein the disease progression index is categorized into one or more stages to depict a stage of Parkinson's disease in the patient.

2. The system of claim 1 wherein the controller is operable to create a patient profile that tracks the disease progression of the patient over a period of time based om the disease progression index.

3. The system of claim 1 wherein the application software enables remote access of patient profile by a medical professional.

4. A method of measuring progression of Parkinson's disease in a patient, the method comprising:

receiving, by a controller strapped onto the patient's body, location coordinates from:

an arm strap device strapped on to at least one arm of the patient wherein the arm strap device comprises one or more sensors configured to capture location coordinates of an arm movement of the patient;

a leg strap device strapped on to at least one leg of the patient wherein the leg strap device comprises one or more sensors configured to capture location coordinates of a leg movement of the patient;

a hand glove device strapped on to at least one palm of the patient wherein the hand glove device comprises one or more sensors configured to capture location coordinates of a palm movement during a tremulous activity experienced by the patient;

a speech distortion unit operable to record and digitize speech to determine distortion in speech uttered by the patient;

computing, by the controller, a stiffness index for the patient based on the location coordinates pertaining to the arm movement of the patient and according to the formula:

$$stiffnessindex = \left[\frac{\pi * t1}{(\pi - \theta) * t_0}\right] * 100$$

wherein r1 is a trajectory radius of the arm movement from a low point to a high point;

tθ is a time taken by the patient to complete the arm movement from the low point to the high point;

t0 is a reference time taken by a normal person to complete a corresponding arm movement;

θ is an angular displacement of the arm movement;

computing, by the controller, a gait index for the patient based on the location coordinates pertaining to the leg movement of the patient and according to the formula:

$$gaitindex == \frac{\sum_{i=1}^{i=3} \sqrt{(x_i' - xi)^2 + (y_i' - yi)^2 + (z_i' - zi)^2}}{\sqrt{(x_1 - x_3)^2 + (y_1 - y_3)^2 + (z_1 - z_3)^2}}$$

wherein xi, yi, zi are coordinates of PD patient leg while walking (front farthest, on ground and back farthest positions);

xi', yi', zi' are step coordinates during early phases;

y1 and y3 are y-coordinates at min and max values of z-coordinates z1 and z3 are z-coordinates at min and max values of y-coordinates;

computing, by the controller, a tremor index for the patient based on intensity and frequency of the palm movement during tremulous activity experienced by the patient;

computing, by the controller, a speech index for the patient wherein computing the speech index comprises:

comparing the digitized speech from the patient with a model digitized speech;

computing a degree of similarity between the digitized speech and the model digitized speech; and generating a numerical value for the speech index value representing a percentage of speech distortion;

computing, by the controller, a disease progression index for the patient based on the stiffness index, gait index tremor index and speech index, wherein the disease progression index is computed according to the formula:

$$DiseaseProgressionIndex =$$

$$tremorindex * \left[1 + \frac{stiffnessindex}{100}\right] * \left[1 + \frac{gaitindex}{100}\right] * \left[1 + \frac{speechindex}{100}\right]$$

wherein the disease progression index is categorized into one or more stages to depict a stage of Parkinson's disease in the patient.

5. The system of claim 4 wherein the method further comprises creating a patient profile that tracks the disease progression of the patient over a period of time based on the disease progression index.

6. The method of claim 4 wherein the method further comprises enabling, through an application software, remote access of patient profile by a medical professional.

\* \* \* \* \*